United States Patent [19]
Martone et al.

[11] 3,950,648
[45] Apr. 13, 1976

[54] SCINTILLATION CAMERA

[75] Inventors: Ronald J. Martone, Cheshire; Peter G. Mueller, Guilford, both of Conn.; Robert Hindel, Auringen near Weisbaden, Germany

[73] Assignee: Picker Corporation, Cleveland, Ohio

[22] Filed: Aug. 5, 1974

[21] Appl. No.: 494,868

Related U.S. Application Data

[62] Division of Ser. No. 287,623, Sept. 11, 1972.

[52] U.S. Cl. .................. 250/369; 250/252; 250/366
[51] Int. Cl.² ...................... G01T 1/20; G01T 1/164
[58] Field of Search ..................... 250/252, 366, 369

[56] References Cited
UNITED STATES PATENTS

| | | | |
|---|---|---|---|
| 3,723,735 | 3/1973 | Spelha et al. | 250/366 |
| 3,732,419 | 5/1973 | Kulberg et al. | 250/369 |
| 3,862,425 | 1/1975 | Myers | 250/369 |

*Primary Examiner*—Archie R. Borchelt
*Attorney, Agent, or Firm*—Watts, Hoffmann, Fisher & Heinke Co.

[57] ABSTRACT

In a gamma ray imaging camera having a scintillation crystal and a plurality of phototubes, two channels are provided for receiving and processing radiation of two different energy levels arising from injection into a patient of two different radioisotopes. Signals in the two energy ranges may both be recorded for future analysis or may be displayed side-by-side on an oscilloscope.

Regardless of whether one or two isotopes are used, information describing the locations of scintillation in the crystal may be digitized, recorded, and played back for visual display at a later time. Alternatively, the location information may be displayed immediately.

Calibration means are also provided for presenting the output of each phototube individually on an oscilloscope so that the apparatus may be adjusted to correct for variations inherent in phototubes.

8 Claims, 7 Drawing Figures

SCINTILLATION CAMERA

CROSS-REFERENCES TO RELATED PATENTS AND APPLICATIONS

This is a division of application Ser. No. 287,623, filed Sept. 11, 1972.

1. U.S. Pat. No. Re. 26,014 issued May 3, 1966 to J. B. Stickney et al, reissue of U.S. Letters Pat. No. 3,070,695 dated Dec. 25, 1962 entitled "Scintillation Scanner."
2. U.S. Pat. No. 3,683,284, issued Aug. 8, 1972, to Peter G. Mueller entitled "Pulse Height Analyser."
3. U.S. Pat. No. 3,532,927, issued Oct. 6, 1970, to Robert Hindel entitled "Scintillation Detector Indicating System."
4. U.S. Pat. No. 3,697,753, issued Oct. 10, 1972, to Ronald J. Martone et al for "Scintillation Camera System."
5. U.S. Pat. No. 3,718,833, issued on Feb. 27, 1973, by Ronald J. Martone et al for "Scintillation Camera System."
6. U.S. Pat. No. 3,601,799, issued on Aug. 24, 1971 by Ronald J. Martone et al for "Digital Recording-Playback Technique"

BACKGROUND OF THE INVENTION

1. Field of the Invention

This invention pertains to gamma imaging devices and more particularly to that class of device known as scintillation cameras.

In the diagnosis of certain illnesses, radioactive isotopes are administered to patients. Many administered isotopes have the characteristic of concentrating in certain types of tissue and either not concentrating in or concentrating to a lesser degree in other types of tissue. For example, iodine 131 collects in thyroid glands. A graphic image produced to show the spatial distribution and concentration of this isotope in the thyroid gland provides an image of the thyroid gland itself. This image is useful in diagnosing a patient's physical condition.

2. Summary of the Prior Art

Generally speaking, the devices used for producing graphic images of the distribution of an isotope in a subject are known as scanners and cameras. With a scanner, a scintillation probe is moved rectilinearly along a plurality of spaced parallel paths. The energy detected is utilized to make either a photographic or a dot image reflecting the spatial distribution and concentration of the isotope in the subject. A clinically successful scanner is described in greater detail in the above-referenced U.S. Letters Pat. No. Re. 26,014 to J. B. Stickney et al.

The devices known as cameras remain stationary with respect to the patient as the graphic image of the spatial distribution of an isotope is developed. Many cameras use an instrument where a relatively large disc-like scintillation crystal is positioned to be bombarded by gamma radiation emitted by a patient. With most cameras, a collimater is interposed between the patient and the crystal. The crystal converts the gamma ray energy impinging on it to light energy. This light energy is in the form of light flashes or scintillations. In one class of camera, a thalium-activated sodium iodide crystal is typically utilized. Since sodium iodide is highly hygroscopic, it is encapsulated with an hermetically sealed envelope. A plurality of phototubes are positioned near the crystal. When a phototube detects a scintillation, an electrical signal is emitted by the phototube. The electrical signal emitted by the phototube is of an intensity which is proportional both to the intensity of the light flash and its distance from the phototube.

Signals emitted simultaneously by the camera phototubes are amplified and then conducted to electronic circuitry. The preferred circuitry is described in greater detail in the referenced applications. This circuitry includes a pulse-height analyzer to determine whether ot not the signals in question reflect the occurrence of a so-called photopeak event. Summing and ratio circuits are included which result in the signal being sent to an oscilloscope to cause a light signal to be emitted by the oscilloscope. The objective is that the oscilloscope signals be displaced relatively each at a location corresponding to the location of a corresponding scintillation in the crystal.

It is a general object of the present invention to provide a more versatile camera than has heretofore been available.

It is a more specific object to provide such an instrument that is capable of resolving radiation emanating from either one or both of two radioactive isotopes and displaying a graphic image of the spatial distribution of radiation from either isotope or of both isotopes.

It is a further object to provide an instrument that incorporates recording and playback apparatus, and that incorporates an improved technique for calibrating the phototube section of the instrument.

SUMMARY OF THE INVENTION

Output signals from the nineteen photomultipliers comprising the detector assembly are provided to decoding matrices whose output signals represent the location of the scintillation in terms of X+, X−, Y+ and Y− location signals. A Z signal is also provided that represents the sum of the outputs of all of the phototubes. Means are also provided in connection with the decoding matrices for selecting any one of the phototube outputs for calibration purposes.

The decoded position signals are then supplied to two analog computers, which are adjusted to accept signals resulting from scintillations having two different energy levels. Thus, one channel may be adjusted to accept signals resulting from radiation by one isotope, and the other channel adjusted to accept radiation from a second isotope. The four X and Y signals from either channel are then combined and converted into a single X signal and a single Y signal.

In one mode of operation, the X and Y position indicating signals are converted to digital signals, which may be recorded on a magnetic medium for future reference. Those digital signals are also reconverted to analog signals for display purposes. The latter analog signals are provided to a rotator, which mixes them in sine/cosine weights to rotate the image being displayed in accordance with the viewer's preferences. The signals are also supplied to a data processor where additional operations may be performed on them.

In another mode of operation, the X and Y signals are not converted into digital signals, but rather are supplied directly to the rotator and then displayed. In that mode of operation, the signals are not recorded and hence are lost so far as future reference is concerned.

In a third mode of operation, signals are sent from any selected one of the various phototubes directly to the data processor. The data processor operates on those signals and displays the gamma ray spectrum of pulses from the particular detector selected. This mode of operation is used for calibration purposes.

Circuitry is provided in conjunction with the display oscilloscopes to permit the display of information from both isotope channels on the oscilloscope in side-by-side relationship. Alternately, information from only of the channels can be presented. The technique of displaying information from both channels, however, has been found to provide a valuable diagnostic tool.

DESCRIPTION OF A PREFERRED EMBODIMENT

It was mentioned in the introduction that a camera embodying the present invention can operate in at least three modes. The first of these, which is designated the "normal" mode, is the most commonly used and is the most complex so far as the interrelationship of parts and signals are concerned. The second mode, which is known as the "fast analog" mode, does not utilize the digitizing and recording portion of the apparatus, and hence is much simpler in its operation. A "test" mode is utilized for calibrating the individual phototubes comprising the detector assembly. A "playback" mode involves playing back information recorded on a magnetic medium and does not require the use of a great many of the components utilized in one normal mode of operation. Therefore, the normal mode operation will be described in detail and the other modes described considerably more briefly.

Figure 1:
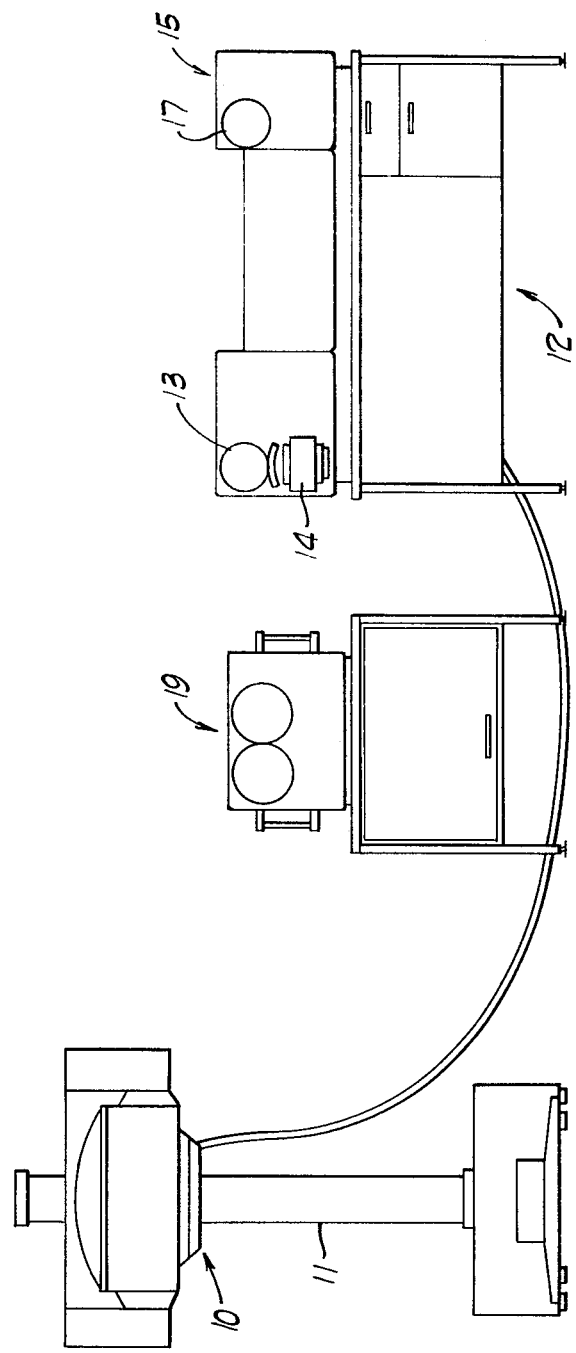
FIG. 1 is an elevational view of a camera and associated consoles utilizing the invention.

In FIG. 1, the detector head is shown generally at 10. The head is adjustably mounted on a stand 11 for positioning adjacent a patient or other subject. Electrical signals from the head 10 are conducted to circuitry contained within the console shown generally at 12.

The signals, after processing by the circuitry, produce a graphic image of the subject under investigation on a monitor oscilloscope 13. A duplicate image is produced on a camera oscilloscope, not shown, which is viewed and photographed by a camera 14.

The circuitry in the console 12 first produces analog signals in manners to be more completely described hereinafter. Assuming the analog signals represent photopeak events, they are digitized. The digital signals may be fed to a computer for analysis and diagnosis.

The digital information is also fed to a built-in data processor 15. This processor utilizes the digital information to generate a variable-width profile histogram of counts versus horizontal distance or a histogram of counts versus time. Such histograms are displayed on a monitor oscilloscope 17. The digital information is also fed to a tape recording console shown generally at 19 for storage and subsequent utilization. The digital information is reconverted to analog form to produce the images displayed on the monitor oscilloscope 13 and recorded by the camera 14.

Figure 5:
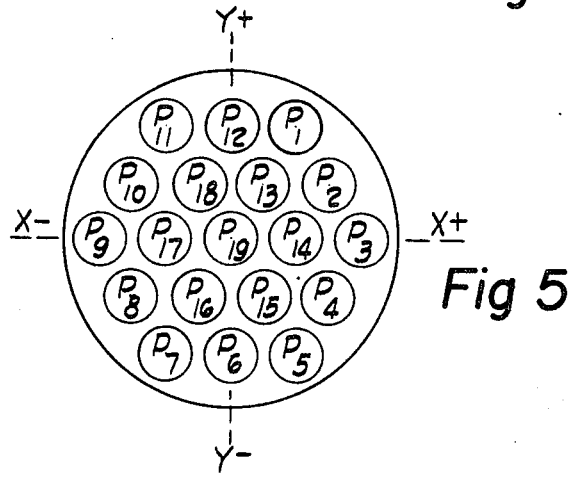
FIG. 5 is a diagrammatic representation of the arrangement of phototubes in the detector head of the camera.

The detector head 10 is shown and described in detail in U.S. Pat. No. 3,683,180, issued on Aug. 8, 1972, to Ronald J. Martone et al. An arrangement of phototubes in the detector head is also shown diagrammatically in FIG. 5 of the present application as comprising a plurality of phototubes P1 – P19. The phototubes P1 – P19 are arranged in an hexagonal array. Certain ones of the phototubes are utilized to determine the location of a scintillation in terms of X+, X–, Y+ and Y– coordinates. Also, the output signals from all of the phototubes P1 – P19 are summed to provide a Z signal. This will become more apparent from the description of FIG. 2.

The signals from the 19 phototubes P1 – P19 are respectively amplified in 19 preamplifiers contained in a preamplifier assembly 20 located in the detector head, and then attenuated to various degrees in an attenuator assembly 22 located in the console 12. The attenuator assembly 22 will be described in greater detail in connection with FIG. 3. However, its primary purpose is to provide for calibrating the various phototubes which may differ in their individual gain characteristics.

From the attenuator assembly 22, the 19 signals are supplied to a decoding assembly 24 comprising six matrices labeled 24a – 24f. The output signals of the decoding matrices 24a, b, c, d, e, are supplied as input signals to two analog computers 26A, 26B connected in parallel.

Te matrix section 24f includes a selector switch (not shown in FIG. 2), which permits the output of any one of the 19 phototubes in the detector assembly 10 to be routed through a test switch 28 and provided on a load 30 to the data processor 15 for calibration purposes. This feature of the invention will be described in more detail hereinafter.

Inasmuch as the two analog computers 26A, 26B are identical in construction, only the computer 26A will be described in detail.

The input signals to the analog computers 26A, 26B from the decoding matrices 24a – e are respectively provided to five variable gain amplifiers 32a – e. The gains of all five of the amplifiers 32a – e are remotely controlled from the front panel of the apparatus to permit receiving scintillations having different energy ranges. The amplifiers 32 are fully illustrated and described in the referenced U.S. Pat. No. 3,601,799, issued on Aug. 24, 1971, to Ronald J. Martone et al.

Output signals from the amplifiers 32a – e are respectively provided to pulse stretchers 34a – e, and the output from the amplifier 32a is also supplied as an input to a pulse height analyzer 36. Each analog computer 26 also contains a ratio detector circuit 38. The pulse height analyzer 36 is shown and described in the referenced patent application Ser. No. 739,793, and the pulse stretchers 34 and the ratio detector 38 are similarly described in the referenced patent application Ser. No. 739,889. Reference is made to those two applications for a complete description of the components 34, 36, 38 comprising each of the analog computers 26A, 26B.

Suffice it to say, that on a lead 40b is present a signal that accurately represents the X+ position of a scintillation occurring in the scintillator, on a lead 40c is a signal accurately representing the X— coordinate of such a signal, on a lead 40d is a similar signal representing the Y+ coordinate, and on a lead 40e is a similar signal representing the Y— coordinate. Similar signals are provided on those leads from the channel B analog computer 26B. Gating means (not shown) are provided to insure that signals are not received simultaneously from both channels A and B. More specifically, if signals are being received from channel A, channel B is effectively disabled. In other words, only one channel is in control.

A timing circuit 42 receives signals on a lead 44 from the ratio detectors 38 in both channel A and channel B analog computers, and on a lead 46 from both pulse height analyzers 36 in those channels. Input pulses are also provided to the timing circuit 42 on a lead 48 from a transfer gate 50 and on a lead 52 from a one-shot multivibrator to be later described. The timing circuit also sends a signal directly to that multivibrator when in the fast analog mode of operation. The timing circuit 42 waits for a signal on the lead 52 indicating the end of a cycle and then gives a reset signal to each pulse height analyzer 36. It also provides a clear signal for the transfer gate 50 on a lead 54. The timing circuit 42 also provides enabling signals to other portions of the analog-to-digital conversion circuitry on a lead 56. These will be described later in more detail.

The four output signals from the stretchers 34b – e are provided to two differential amplifiers 58X, 58Y. The X+ and X— signals on the leads 40b, 40c are provided to the amplifier 58X, and the Y+ and Y— signals on the leads 40d, 40e are provided to the amplifier 58Y. Each of these amplifiers 58X, 58Y combines its respective input signals and provides single output signals respectively representing X and Y location coordinates. The X coordinates from the output of the amplifier 58X are provided to a height-to-time converter 60X, and the Y coordinate information is provided from the Y differential amplifier 58Y to a height-to-time converter 60Y.

The X and Y coordinate information is also repectively provided on leads 62X, 62Y to an additional component of the circuitry not yet described.

The height-to-time converters 60X, 60Y are conventional components that produce gating pulses of constant predetermined amplitudes, whose lengths are proportional to the amplitudes of the input signals to the converters. The output signals of the converter 60X, whose time durations are proportional to the amplitudes of the input signals from the differential amplifier 58X, are provided to a gate 62X. Similarly, th output of the converter 60Y is provided to a gate 62Y. Second inputs to the gates 62X, 62Y are provided from an oscillator 64. The oscillator is actuated by the gating signals from either of the converters 60X, 60Y, and provides a train of pulses in which the number of pulses is controlled by the longest output pulse from either of the converters 60X, 60Y. At the end of the signal from the converter 60X, the gate 62X is closed, even though the output pulse from the converter 60Y may not yet have terminated. When the longer of the pulses from the converter 60X, 60Y terminates, the oscillator 64 is shut off and both gates 62X and 62Y are closed. The result is that a train of output pulses is provided from the gate 62X that is proportional in number to the height of the output pulse of the differential amplifier 58X, and a train of pulses is provided from the gate 62Y that is proportional in number to the height of the output pulse from the differential amplifier 58Y.

The construction and function of the converters 60X, 60Y, the oscillator 64, and the gates 62X, 62Y are comparable to those described in an article by D. H. Wilkinson, entitled "A Stable Niney-Nine Channel Pulse Amplitude Analyzer for Slow Counting," proceedings Cambridge Philosophical Society, Volume 46, Part III, pgs. 508–518 (1950).

The output signals from the gates 62X, 62Y are respectively provided to scalers 66X, 66Y. The scalers serve to store the numbers of pulses which numbers are proportional in amplitude to the X and Y output signals of the differential amplifiers 58X, 58Y, respectively. The scaler 66 also contains a section 66F that receives and stores flag signals from the pulse height analyzers 36 in the channel A and channel B analog computers 26A, 26B that indicate from which of the two channels the signals being stored are received.

The digital signals stored in the X scaler 66X, the Y scaler 66Y and the flag portion 66F are transferrable through a gate 68 to a shift register 70. The gate 68 is opened in response to a signal from the transfer gate 50. The transfer gate 50 provides that signal to open the gate 68 when coincidence occurs between the clear signal received from the timing circuit 42 on the lead 54 and the signal received on lead 73 from a ring counter 72.

The ring counter 72 is shown and described in detail in U.S. Pat. No. 3,601,799, issued on Aug. 24, 1971. In addition to the circuitry shown in that application, the ring counter 72 is also connected to the oscillator 64 by means of a lead 74. As set forth in the referenced U.S. Pat. No. 3,601,799, issued on Aug. 24, 1971. The ring counter has 24 different intervals. These various intervals provide timing signals that control various components of the apparatus. The ring counter 72 sends a signal on a lead 73 to the transfer gate 50 indicating when information should be transferred from the scaler 66 to the shift register 70. It also sends a signal to a record amplifier 76 that indicates when digital information should be recorded by a video recorder 78. A similar signal is sent to the shift register 70 that enables it to transfer information to the recorder 78 through the record amplifier 76. An additional signal is sent to a gate 80 that in turn controls a transfer gate 82 between the shift register 70 and a display register 84. It is pointed out that both the X and Y digitized signals, as well as the flag signal, are stored in the shift register 70 and are transferred through the gate 82 to the display register 84.

The signal from the gate 80 that is sent to the gate 82 is also sent through a delay circuit 85 to a one-shot flip-flop 86 along with the signal from the timing circuit 42. The flip-flop 86 generates a signal that is provided to an intensification control 88 and, at the termination of that signal, also generates a signal that is returned to the timing circuitry 42 on the lead 52 to cause the timing circuit to generate a signal to reset the pulse height analyzer 36 in each analog computer 26A, 26B. The intensification control is a front panel adjustment.

The X and Y coordinate signals in the display register 84 are supplied to a digital-to-analog converter 90 which reconverts them into X and Y analog signals. Because the signals supplied to the converter 90 are in digital form, they will, if displayed on an oscilloscope, cause the beam of the oscilloscope to assume certain definite discrete positions. This will present a dot-like pattern on the screen of the oscilloscope that may well be objectionable to a viewer. For this reason, that pattern is eliminated by providing a smoothing generator 92 that causes the dots to tend to flow together and present a much more continuous pattern than is otherwise possible. The smoothing generator 92 is shown and described in referenced U.S. Pat. No. 3,718,833, issued on Feb. 27, 1973.

The X and Y analog signals are provided from the converter 90 through appropriate gating means (not shown) to a rotator 94. Signals from the differential amplifiers 58X, 58Y may also be supplied on the leads 62X, 62Y through similar gating means to the rotator. It is, of course, imperative the signals be supplied only from the converter 90 or from the differential amplifier 58 at any one time and that signals not be supplied simultaneously from both.

The rotator 94 is controlled by a front panel adjustment on the console, and mixes the X and Y signals in sine/cosine weights to rotate the image being displayed in accordance with the viewer's preference. The rotator 94 may comprise a resistor matrix for enabling the rotation of the image on the oscilloscope 13 by fixed predetermined increments. This involves the use of a selector switch (front panel) to select a particular resistor combination. The selection of the resistor values for such a matrix is based on a formula that relates the output of the matrix into a fixed input impedance and a desired rotation of the axis about its origin. This formula, which includes sine and cosine terms, is as follows:

$$X_{out} = X_{in} \cos \phi - Y_{in} \sin \phi;$$
and
$$Y_{out} = X_{in} \sin \phi + Y_{in} \cos \phi$$

The resistors supply the values for the sine/cosine functions.

Alternatively, the rotator 94 may comprise a sine/cosine resolver, which will provide continuous rotation of the image by any desired amount rather than by fixed increments. In either case, the output of the rotator 94 will comprise four signals rather than two. Those four signals represent X+, X−, Y+ and Y− coordinates of a scintillation.

The four signals from the rotator 94 are supplied to a pair of differential amplifiers 96, which again convert them to two signals representing the X and Y coordinates of location of the scintillation occurring in the scintillator. The output signals of the differential amplifiers 96 are supplied to a multiplexer 98 and to a dual display control 100.

The multiplexer 98 also receives signals from the decoding matrix section 24F through the test switch 28 on the lead 30. The multiplexer 98 is essentially a switching circuit which selects the appropriate signal to be sent to the data processor 15 depending on the mode of operation selected by the operator. It, of course, depends on the setting of the front panel control that determines the mode of operation desired.

Normally, the dual display control 100 has no effect on the operation of the apparatus and the signals from the differential amplifiers 96 merely pass through it for display on the oscilloscope 13. However, when a front panel selector switch (not shown) is set to indicate a dual isotope type of operation, the dual display control 100 comes into operation. In that case, the control 100 serves to attenuate the Y signal by a factor of two. The X signal is also attenuated by a factor of two and shifted to the right or to the left depending on the presence of a flag provided to the control from the display register 84 on a lead 102. If a flag is present, which indicates that the signal is due to isotope A, the X signal is shifted to the left. If a flag is not present, which indicates that the signal is due to isotope B, the signal is shifted to the right, or vice versa depending on the design of the equipment.

Figure 3A:
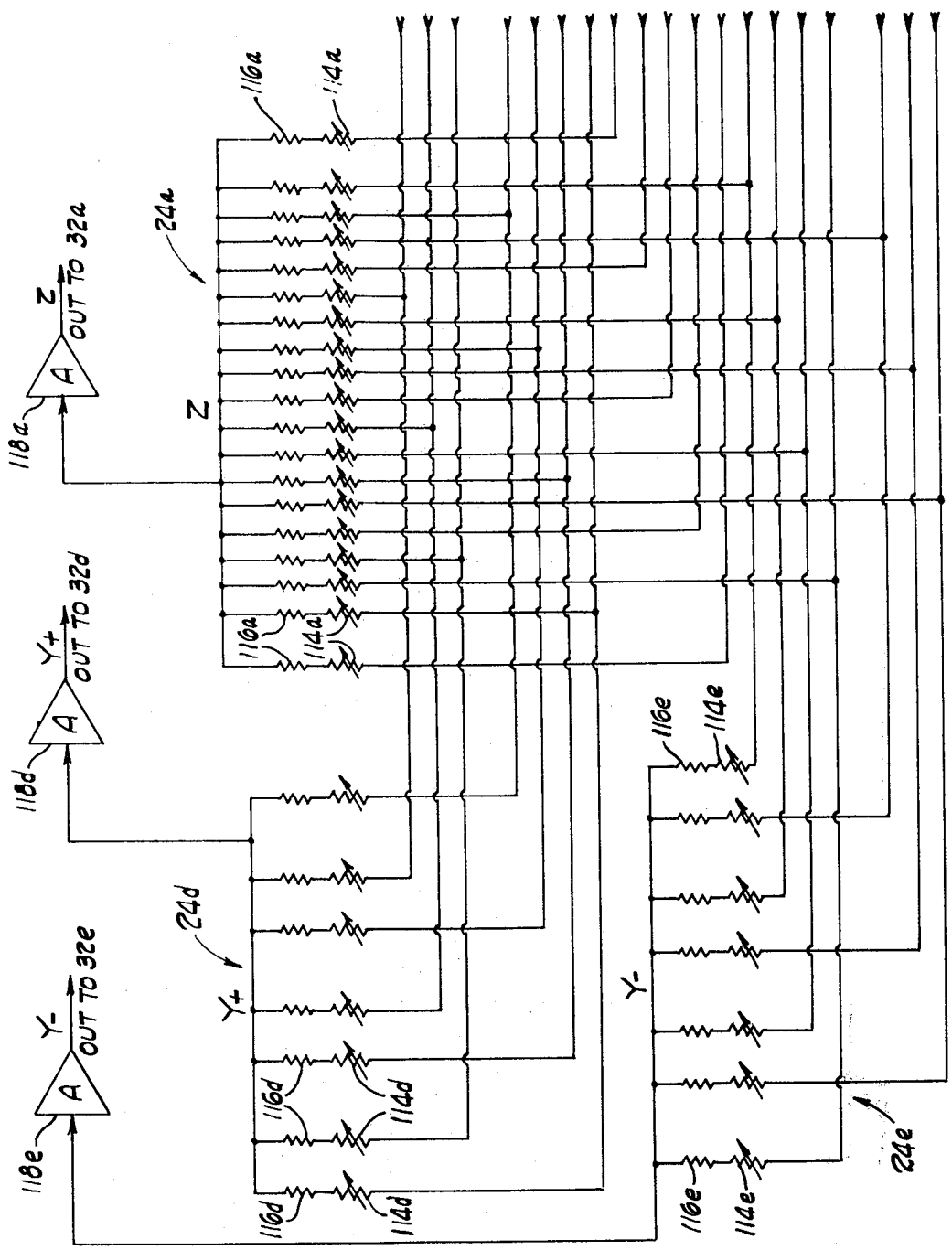
FIGS. 3A and 3B are a combined circuit and block diagram of attenuators and decoding matrices that provide input signals to the analog computers.
Figure 3B:
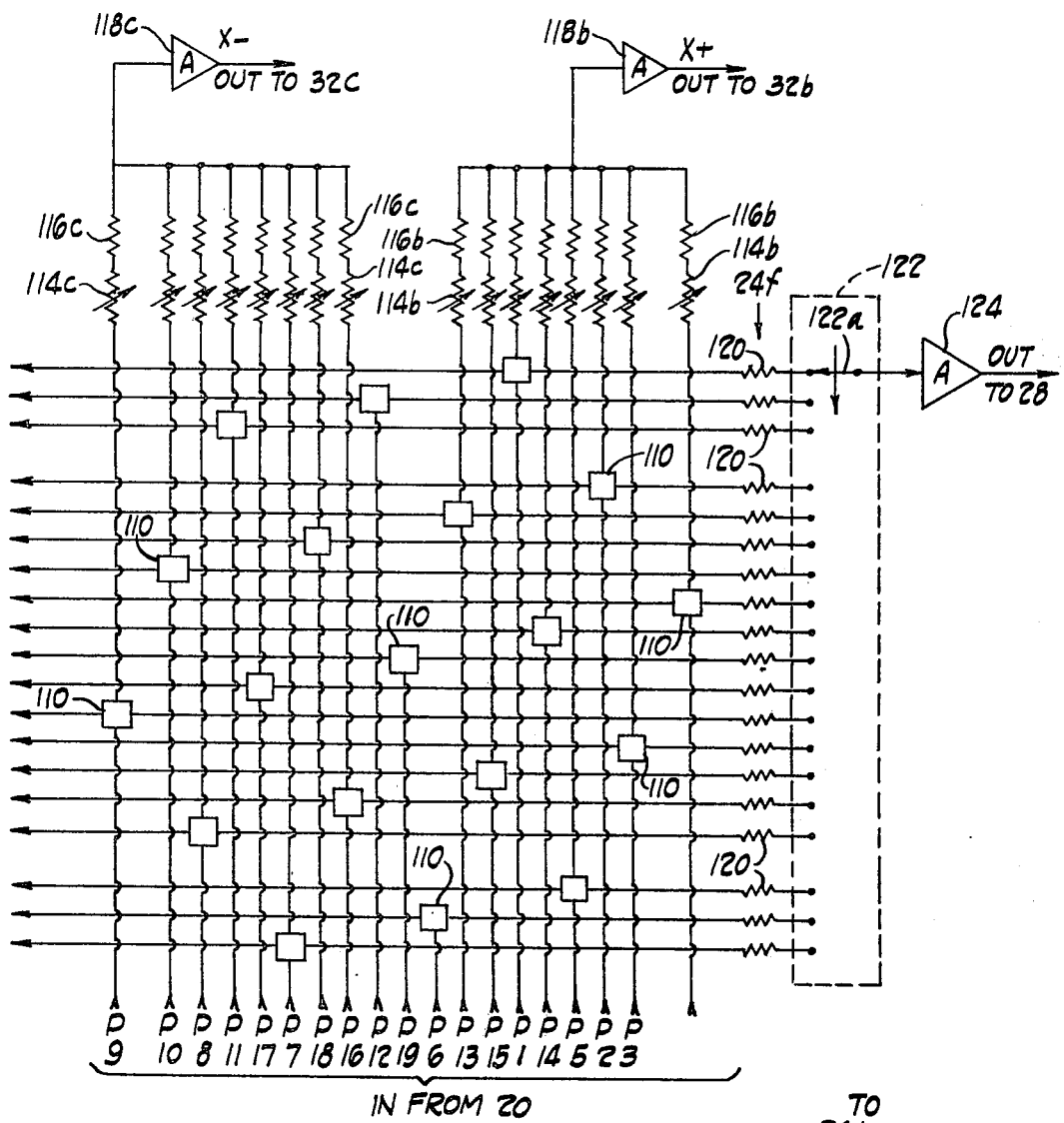
Figure 4:
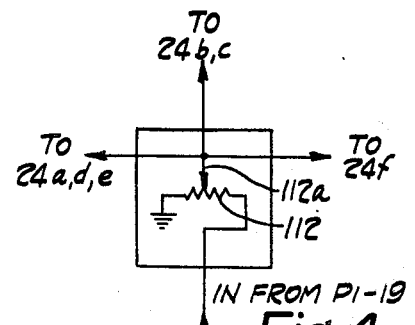
FIG. 4 is a schematic diagram of an attenuator used in the diagram of the FIG. 2.

FIGS. 3A and 3B illustrate the attenuator 22 and the decoding matrices 24. As shown in FIG. 3B, 19 input lines labeled P1 – P19 are provided from the 19 phototubes shown in FIG. 5. Each of these input leads is provided to an attenuator 110, which is shown as a block in FIG. 3B. FIG. 4 illustrates the construction of each attenuator 110.

As shown in FIG. 1, the attenuator 110 comprises a potentiometer 112, one end of which is connected to one of the input lines from a phototube P1 – P19 and the other end of which is grounded. A movable arm 112a of the potentiometer 112 provides an output to all six of the matrices 24a – f. By adjusting the arm 112a of the potentiometer, the signals provided to all six of the decoding matrices 24 are varied by the same amount.

Signals from all of the attenuators 110 are provided to the Z signal decoding matrix 24a. Each signal is supplied through a variable resistor 114 and a fixed resistor 116 to a summing amplifier 118. The variable resistors 114 provide calibration means for each phototube output so far as the Z signal is concerned.

Signals from the attenuators 110 corresponding to those received from phototubes lying on the X+ side of the Y axis are provided to the matrix 24b. As shown, these include signals which are provided from the phototubes P13, P15, P1, P14, P5, P2 and P3. These signals are respectively supplied through variable resistors 114b and fixed resistors 116b to a summing amplifier 118b. The values of the resistors 116b are weighted in accordance with the distance of the particular phototube involved from the Y axis. For example, if the phototube P3 is twice as far from the Y axis as the phototube P14, the resistor 116b receiving the signal from the phototube P3 would have one-half the value of the resistor receiving the signal from the phototube P14. The variable resistors 114b provide individual calibration for the phototubes enumerated.

Similarly, signals from the phototubes P9, P10, P8, P11, P17, P7, P18 and P16 are supplied through variable resistors 114c and fixed resistors 116c to the input of a summing amplifier 118c. The output of the summing amplifier 118c represents the X− signal. The resistors 116c are weighted in accordance with the location of their corresponding phototube in the same manner as the resistors 116b.

In a similar manner, signals from the phototubes P11, P12, P1, P10, P18, P13 and P2 are provided through variable resistors 114d and fixed resistors 116d to a summing amplifier 118d. The output of the amplifier 118d represents the Y+ output signal. Y− output signals are provided from the matrix 24e in a similar manner through variable resistors 114e and fixed resistors 116e. Those signals are, of course, provided from the phototubes P8, P16, P15, P4, P7, P6 and P5. Needless to say, the resistors 116d, 116e are weighted in the same manner as those previously mentioned, but in accordance with the distance of the corresponding phototubes from the X axis.

Figure 2A:
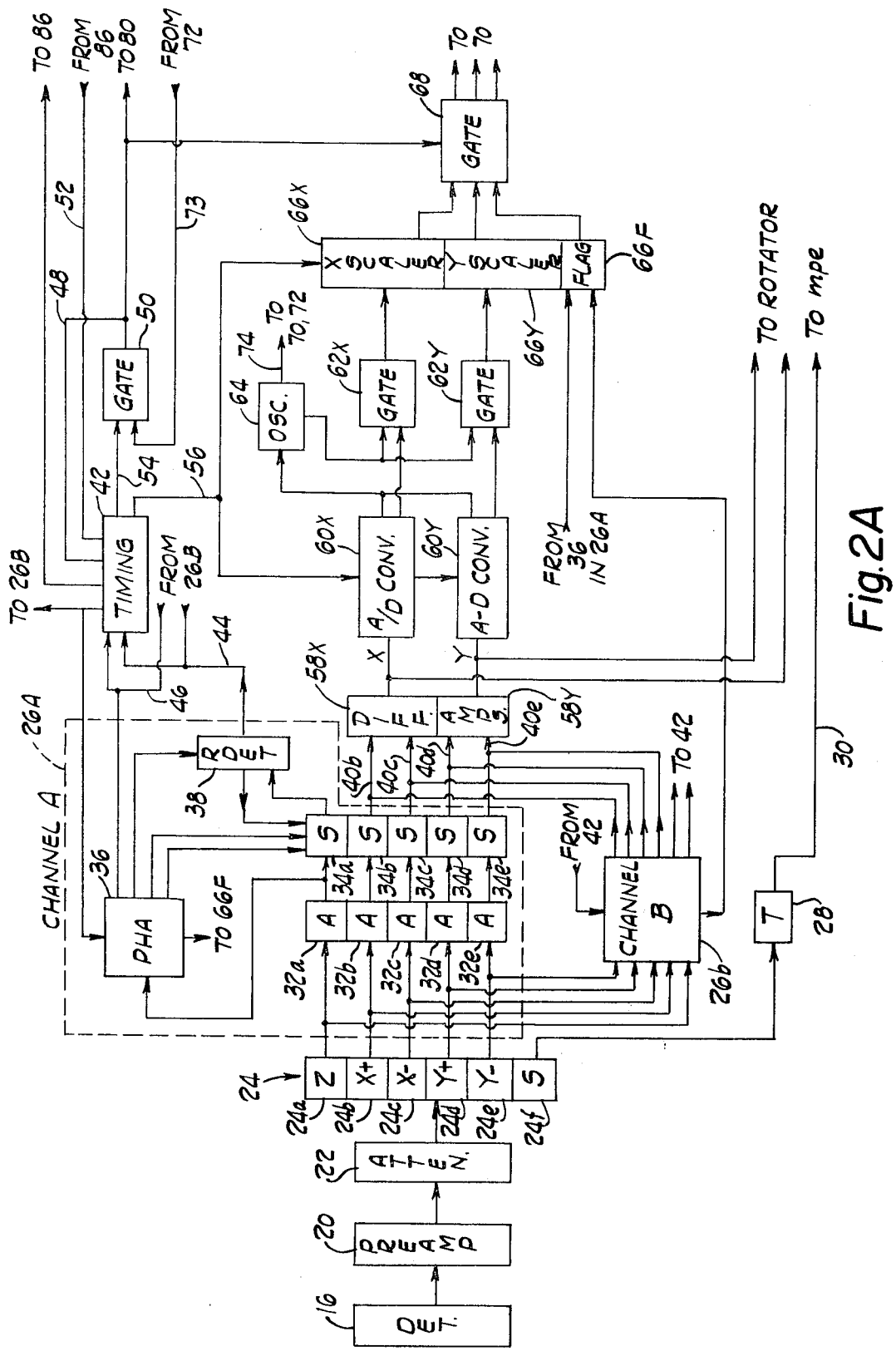
FIGS. 2A and 2B are block diagrams of a camera system embodying the invention.

Signals from the attenuators 110 are also provided through fixed resistors 120 to 19 contacts of the selector switch 122. The selector switch has a movable arm 122a that can connect any one of the 19 contacts to the input of an amplifier 124. The output of the amplifier 124 is provided through the test switch 28 to the multiplexer 98, both of which are shown in FIG. 2. Thus, by virtue of the attenuators 110 and the individual calibration controls 116, the outputs of all of the phototubes P1 – P19 and their preamplifiers 20 can be adjusted to provide for variations in gain of any of the phototubes or preamplifiers.

Figure 2B:
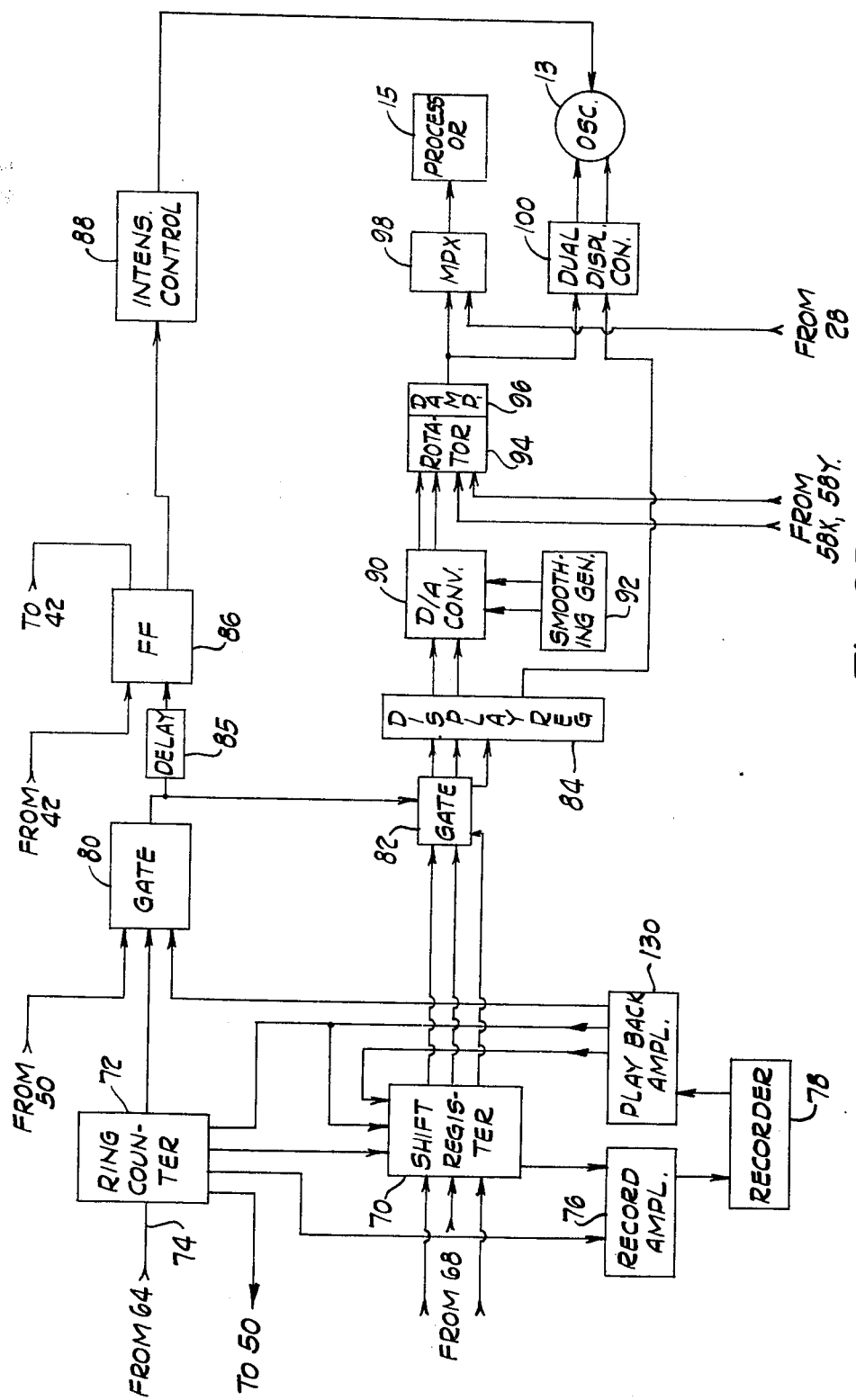

The data processor 15 shown in FIG. 2B may be any one of various makes or types. However, it has been found in practice that a processor known as the Spectron 100, which is available from Picker Corporation, White Plains, New York, is preferable in this particular application. It embodies an oscilloscope on which the various desired histograms are displayed, and which also serves as a calibration indicator when calibrating the phototubes. Reference is made to the instruction manuals of that equipment for further details.

In the tape playback mode of operation, only the recorder 78 and a playback amplifier 130 are utilized, along with the succeeding circuitry shown in FIG. 2B. The playback amplifier 130 provides a signal to the gate 80 and to the ring counter 72 to indicate that the equipment is in a playback mode of operation. The recorded signals are supplied to the shift register 70. The functions of those portions of the equipment are shown and described in the referenced U.S. Pat. No. 3,601,799, issued on Aug. 24, 1971. The remainder of the circuitry functions as described in the description of normal mode of operation.

In the fast analog mode of operation, the entire analog-to-digital-to-analog portions of the apparatus are not utilized. This includes the converters 60, the gates 62, the oscilloscope 64, the transfer gate 50, the ring control 72, the gate 80, the shift register 70, the record and playback amplifier 76 and 130, the delay 85, the flip-flop 86, the display register 84, the digital-to-analog converter 90 and the smoothing generator 92. In the fast analog mode of operation, signals representing X and Y coordinates are transferred directly from the differential amplifiers 58X and 58Y to the rotator 94 on the leads 62X, 62Y and are provided from the rotator through the multiplexer 98 to the data processor 15 and to the oscilloscope 13 through the dual display control 100.

We claim:

1. In a device for producing a visual display representing the spatial distribution of incident stimuli from a subject under investigation, said device including a light-emitting element for emitting flashes of light in response to such incident stimuli and a plurality of light-responsive components each of which is responsive to the light flashes to emit analog electrical signals with such signals each having an amplitude which is a function of the responsivity of said light responsive component and the intensity of the light signal the improvement comprising:
   a. a selector for electrically isolating the analog signals emitted by at least one selected light-responsive component; and
   b. a processor for controlling the amplitude of each of said selectable components to enable calibration of the relative amplitudes of the analog signals from the selectable components so that the device has a uniform response to stimuli independent of variations in the responsivity of said light-responsive components.

2. The improvement of claim 1, wherein said processor includes variable circuitry for independently attenuating said analog signals from each of said light-responsive components to provide said calibration enablement.

3. An apparatus for use in a system for producing a visual display representative of the spatial distribution of incident stimuli from a subject, said system including a light emitting element for emitting flashes of light in response to such incident stimuli and a plurality of light responsive components optically coupled to said light emitting element, each of said light responsive components having an output emitting analog electrical signals in response to light incident thereon, such analog electrical signals each having an amplitude which is a function of the intensity of the light to which the emission of said electrical signal is responsive, said apparatus comprising:
   a. a sensor for producing a separate indication of the amplitude of said analog electrical signals from one of said components when the output of that light responsive component is connected to said sensor,
   b. a selector for selectively coupling the output of each of a plurality of said light responsive components to said sensor, and
   c. an attenuator connectable to each of a plurality of said outputs of said light emitting components for controlling the amplitudes of said analog electrical signals generated by said light responsive components to enable calibration of the relative outputs from said light responsive components according to the indication by said sensor of the relative amplitude of said electrical output signals.

4. The apparatus of claim 3, wherein said attenuator comprises a potentiometer.

5. The apparatus of claim 3, wherein said system further includes a plurality of decoding matrices, each of said decoding matrices being connected to receive the outputs of a plurality of said light responsive components, and wherein said apparatus further comprises:
   said attenuator being connected to simultaneously control the amplitude of the electrical signals emitted by each of said light responsive components which is transmitted to said plurality of decoding matrices.

6. Th apparatus of claim 3, wherein said system further comprises a summing matrix connected to the outputs of each of said light responsive components for producing a signal which is a function of the total amplitude of all of the outputs of said light responsive components, and said apparatus further comprises:
   said attenuator being connected to control the amplitude of each of said electrical signals transmitted to said summing matrix.

7. The apparatus of claim 3, wherein said system further includes an amplifier connected to each of said outputs of said light responsive components, said apparatus further comprising:
   the outputs of each of said amplifies being selectively connectable to said sensor for permitting the calibration of said outputs of said amplifiers.

8. An apparatus for producing a visual display representative of the spatial distribution of incident stimuli of at least two different energy ranges emanating from a subject, said apparatus comprising:

a. a detector for generating signals in response to the occurrence of said stimuli, said signals each bearing information relating to the energy level and location of the stimulus to which it is responsive;

b. indication means to identify each of said signals representing an incident stimulus having an energy level in a predetermined range, and c. a display apparatus connected to receive said signals, and to display one image representing the location information borne by said identified signals, and a separate image of the location information borne by those signals not so identified.

* * * * *